United States Patent
Freeman et al.

(10) Patent No.: US 10,064,652 B2
(45) Date of Patent: Sep. 4, 2018

(54) APPARATUS FOR CONDUCTING AN EPISIOTOMY AND METHOD OF USING THE SAME

(75) Inventors: Robert Freeman, Plymouth (GB);
Heidi Hollands, Plymouth (GB);
Laurie Barron, Plymouth (GB);
Dharmesh S. Kapoor, Plymouth (GB)

(73) Assignee: Plymouth Hospitals NHS Trust,
Plymouth, Devon (GB)

( * ) Notice: Subject to any disclaimer, the term of this patent is extended or adjusted under 35 U.S.C. 154(b) by 420 days.

(21) Appl. No.: 14/118,005

(22) PCT Filed: May 14, 2012

(86) PCT No.: PCT/GB2012/000428
§ 371 (c)(1),
(2), (4) Date: Feb. 3, 2014

(87) PCT Pub. No.: WO2012/156662
PCT Pub. Date: Nov. 22, 2012

(65) Prior Publication Data
US 2014/0378990 A1 Dec. 25, 2014

(30) Foreign Application Priority Data
May 17, 2011 (GB) .................................. 1108250.0

(51) Int. Cl.
*A61B 17/42* (2006.01)
*A61B 17/3201* (2006.01)
*A61B 17/32* (2006.01)

(52) U.S. Cl.
CPC .......... *A61B 17/42* (2013.01); *A61B 17/3201* (2013.01); *A61B 2017/320052* (2013.01)

(58) Field of Classification Search
CPC ........ A61B 17/3201; A61B 17/320016; A61B 17/29; A61B 17/295; A61B 17/42;
(Continued)

(56) References Cited

U.S. PATENT DOCUMENTS 178,093 A * 5/1876 Wiggins .................. B26B 29/04
30/233
803,151 A * 10/1905 Coggeshall .............. B25H 7/04
33/631
(Continued)

FOREIGN PATENT DOCUMENTS

CH 359995 1/1962
CN 201213824 5/2008
(Continued)

OTHER PUBLICATIONS

International Search Report, PCT Application No. PCT/GB2012/000428, dated Aug. 7, 2012, 5 pages.

*Primary Examiner* — Eric Rosen
*Assistant Examiner* — Mikail Mannan
(74) *Attorney, Agent, or Firm* — Leydig, Voit & Mayer, Ltd.

(57) ABSTRACT

An episiotomy scissors (2) for use in conducting an episiotomy on a subject is provided, the scissors comprising a pair of pivotably connected scissor members; (4a, 4b) each scissor member comprising a handle (6a, 6b) extending in a proximal direction from the pivot connection and a blade (8a, 8b) extending in a distal direction from the pivot connection; and a guide member (20) mounted to a scissor member and having a guide surface (22a, 22b) extending in a distal direction from the scissor member at an acute angle to the longitudinal axis of the blade of the scissor member.

4 Claims, 5 Drawing Sheets

(58) Field of Classification Search
CPC ............... A61B 17/44; A61B 17/32; A61B 2017/320052; A61B 2017/2926; B26B 13/00; B26B 13/005; B26B 13/02; B26B 13/04; B26B 13/06; B26B 13/08; B26B 13/10; B26B 13/12; B26B 13/14; B26B 13/18; B26B 13/20; B26B 13/22; B26B 13/24; B26B 13/26; B26B 13/28; B26B 13/285
USPC ............ 606/167–180, 205–210; 30/233, 286
See application file for complete search history.

(56) References Cited

U.S. PATENT DOCUMENTS

| | | | | |
|---|---|---|---|---|
| 1,904,399 | A | * | 4/1933 | Balthaser ............ A61B 17/282 30/233 |
| 2,568,234 | A | | 3/1949 | Haufrect |
| 3,078,503 | A | * | 2/1963 | Webb ........................ 452/117 |
| 4,235,016 | A | * | 11/1980 | Kobelt ................ B26B 29/04 30/233 |
| 4,850,110 | A | * | 7/1989 | Meier, Jr. ............. B26B 13/24 30/135 |
| 5,542,435 | A | * | 8/1996 | Kelly et al. ................. 128/846 |
| 2005/0277969 | A1 | * | 12/2005 | Happonen et al. .......... 606/174 |
| 2009/0043323 | A1 | * | 2/2009 | Alleyne ...................... 606/167 |
| 2009/0082796 | A1 | * | 3/2009 | Orilla .................... A61B 17/02 606/167 |
| 2011/0238076 | A1 | * | 9/2011 | Kapoor ....................... 606/119 |

FOREIGN PATENT DOCUMENTS

| | | |
|---|---|---|
| CN | 201192365 | 2/2009 |
| GB | 2451855 A | 2/2009 |
| WO | 2009020660 A | 2/2009 |
| WO | WO2009022149 * | 9/2009 |

* cited by examiner

APPARATUS FOR CONDUCTING AN EPISIOTOMY AND METHOD OF USING THE SAME

This application is a U.S. National Phase application under 35 U.S.C. § 371 of International Application No. PCT/GB2012/000428, filed on May 14, 2012, and claims benefit to British Patent Application No. GB 1108250.0, filed on May 17, 2011. The International Application was published in English on Nov. 22, 2012 as WO 2012/156662 under PCT Article 21(2).

The present invention relates to a device for conducting an episiotomy and to a method of using the same.

During vaginal childbirth, the vaginal opening of the mother becomes highly distended, to accommodate passage of the baby. This distension causes a general displacement of tissue around the vaginal opening of the mother during the birthing procedure. However, this stretching, if insufficient, can result in damage or tearing to the tissue surrounding the vaginal opening.

Faecal/anal incontinence is believed to affect from 5 to 10% of the female adult population. One of the major causes of faecal incontinence in women results from childbirth, and arises from damage to the anal sphincter/valve caused by tearing of the tissue extending between the vaginal opening and the anus (perineum), typically due to a tear in the perineum arising during the actual birth of the child. Such a tear extending from the vaginal opening can result in damage and long term injury to the anal sphincter muscle, in turn giving rise to the aforementioned incontinence.

Episiotomy is a procedure commonly carried out by an obstetrician or midwife during the vaginal birth of a baby. During the procedure, a cut is made into the tissue surrounding the vaginal opening, in order to enlarge the opening and allow the baby to be more easily delivered. It is common practice to administer an episiotomy where there is a high risk that the normal birthing procedure will cause the tissue surrounding the vaginal opening to tear. By making an incision, the object of the episiotomy is to reduce the tissue damage to the anal sphincter which may result from allowing the tissue to tear naturally. In addition, the damage to the tissue resulting from the incision is more easily repaired, for example by suturing, than tissue damage resulting from a natural tear. Finally, and perhaps most importantly, making an incision in the tissue surrounding the vaginal opening before tearing commences allows the direction of the resulting tear to be controlled, avoiding substantial damage to the surrounding tissue that may be very difficult or impossible to repair.

Scissors for performing an episiotomy are known in the art. Thus, U.S. Pat. No. 2,568,234 discloses episiotomy scissors in which the blades extend at an acute angle to the handles of the scissors, with the tip portion of one blade extending laterally to form a guard.

CN 201213824 discloses lateral episiotomy scissors having a particular arrangement of cutting edges on the blades of the scissors. CN 201192365 is concerned with lateral perineotomy scissors, again having a specific arranged of cutting surfaces on the blades thereof.

In general, one of two types of incision is made to the subject during the episiotomy procedure. A midline incision is an incision made along the perineum from the vaginal opening in the direction of the anus, used particularly in the United States. While this form of incision is widely practised, it is associated by the risk that the incision extends during the birthing procedure due to distension of the vaginal opening and damages the tissue surrounding the anus, in particular the anal sphincter muscle. This can in turn lead to the long term anal incontinence discussed above. As an alternative, a lateral incision may be made, in which case a cut is made in the tissue surrounding the vaginal opening in a lateral direction away from the medial line between the vaginal opening and the anus. This is the preferred method used in the United Kingdom. Studies have indicated that the risk of sustaining a third degree tear in the tissue decreases by 50% for every increment of 6° the incision is moved away from the perineal midline. Accordingly, there is strong evidence in support of the use of lateral incisions in the episiotomy procedures.

In practice, it is a relatively simple matter for the medical practitioner (accoucheur) delivering the baby to mark up and/or make an incision along the perineal midline by eye, without the aid of instruments. However, this is not the case when the practitioner is wishing to make a lateral incision. Studies have shown that many midwives and doctors significantly under estimate the angle of a lateral episiotomy incision, leading to the resulting incision being too close to the perineal midline, with the attendant increased risks of a third degree tear and damage to the anal sphincter muscle.

As the birthing procedure proceeds and the head of the baby distends the vaginal opening of the mother, the tissue surrounding the vaginal opening is displaced. This in turn reduces the accuracy of the lateral incision. As a result, an episiotomy conducted after distension of the vaginal opening has begun, in particular when the opening is fully stretched, while appearing at the time of making the incision to be at an appropriate lateral angle, can be found to be close to the perineal midline when the vaginal opening is relaxed after childbirth.

Accordingly, there is a need for a device to aid the medical practitioner in carrying out an episiotomy, in particular in aiding the practitioner to perform an accurate medial incision.

WO 2009/020660 concerns a childbirth instrument and method. In particular, there is disclosed an instrument having one or more elongated reference slots, through which an episiotomy may be conducted. The slots are arranged at the appropriate angles for performing the episiotomy, with the remainder of the instrument acting as a guard to protect the infant.

Perhaps most recently, GB 2,451,855 discloses an episiotomy guide having a guide means for indicating alignment of the guide relative to a line between the vaginal opening and the anus of the mother, thereby to facilitate a lateral episiotomy incision.

As a result of extensive development, it has now been found that a guide surface may be incorporated into an episiotomy scissors, thereby allowing the obstetrician or midwife to quickly align the scissors and perform the episiotomy with the minimum number of devices and minimum amount of time.

Accordingly, in a first aspect, the present invention provides an episiotomy scissors for use in conducting an episiotomy on a subject, the scissors comprising:
  a pair of pivotably connected scissor members;
  each scissor member comprising a handle extending in a proximal direction from the pivot connection and a blade extending in a distal direction from the pivot connection; and
  a guide member mounted to a scissor member and having a guide surface extending in a distal direction from the scissor member at an acute angle to the longitudinal axis of the blade of the scissor member.

The scissors of the present invention comprise a guide member extending from one of the blades of the scissors. The scissors are for performing a mediolateral episiotomy, that is an incision extending from the vaginal opening at an angle to the midline of the perineum. In this respect, an angle of 60° to the midline is particularly preferred. The guide member is used in practice to align the scissors at the correct orientation to the vaginal opening, before the episiotomy incision is made. In particular, the guide member is aligned with the midline of the perineum of the mother. With the guide member so-aligned, the scissors are in the correct orientation and position to perform a mediolateral episiotomy at the correct angle to the midline.

The scissors may have any suitable form. Scissors suitable for performing an episiotomy are known in the art. In one embodiment, the scissors comprises two scissor members in which the handle and the blade extend along a single longitudinal axis, such that when the scissors are closed, the blades and handles lie along a substantially straight line.

Alternatively, the scissors may comprise scissor members in which the handle and the blade extend at an angle to each other. When the scissors are closed, the handles are aligned and extend parallel to each other along a first line and the blades are aligned and extend along a second line at an angle to the first line. One design of scissors of this type is the Barnes scissors, known in the art and commercially available. Braun-Stadler scissors are similarly configured.

The blades of the scissors may be curved or straight. Preferably, the blades are straight.

The scissors of the present invention comprise a guide member. The guide member may be of any suitable form that enables the user to align the scissors for making the required episiotomy incision. In particular to allow the guide member to be aligned with the midline of the perineum of the patient, in turn to align the blades of the scissors at the correct angle for performing a lateral episiotomy incision. For example, the guide member may comprise an opening, such as a slot, the edges of which provide the guide surface for aligning the scissors during use. Preferably, the guide member has an external edge surface for aligning the scissors.

In a particularly preferred embodiment, the guide member is generally elongate. In one preferred embodiment, the guide member has an aspect ratio of at least, 2, preferably at least 3, more preferably at least 5, still more preferably at least 10.

The guide member may be curved along its length. More preferably, the guide member is substantially straight along its length.

The guide member extends from, for example being mounted to, a scissor member. Preferably, the guide member extends from the blade of the scissor member. Alternatively, the guide member may extend from the handle of the scissor member, preferably adjacent the proximal end of the blade.

The guide member extends in a distal direction from the scissor member of the scissors. The guide member may extend from any position on the scissor member that allows it to be aligned with the midline of the perineum of the patient and the appropriate incision performed. Preferably, the guide member extends from the scissor member at a position sufficiently spaced from the distal end of the blade such that the incision of the required length may be formed by a single cut from the scissors. In this respect, the guide member preferably extends from the scissor member at a position at least 40 mm, more preferably at least 50 mm, from the distal end of the blades, thereby allowing an incision of this length to be formed in a single cut.

As noted the guide member preferably extends from a suitable position along the length of the blade. In one embodiment, the guide member extends from a position on the blade between the mid-point of the blade and the pivot connection of the scissors, more preferably a position midway between the pivot connection of the scissors and the mid-point of the blade.

The guide member may be of any suitable length that allows the scissors to be aligned relative to the midline of the perineum. In one embodiment, the guide member is relatively long and extends at least to a line extending from the distal end or point of the blades perpendicular to the longitudinal axis of the handles of the scissors, more preferably beyond the said line. This arrangement may be preferred when the scissors comprise scissor members in which the blade and handle extend along a single straight line. In an alternative embodiment, the guide member is shorter. This arrangement may be preferred when the scissors comprise scissor members in which the handle and blade extend at an angle to one another.

The guide member extends in a distal direction from the scissor member to which it is mounted at an acute angle to the longitudinal axis of the blade. This angle determines the angle at which mediolateral episiotomy is made, once the guide member is aligned with the midline of the perineum of the mother, as described above. This angle is preferably at least 30°, more preferably at least 40°, still more preferably at least 50°. This angle is preferably less than 80°, more preferably less than 75°, still more preferably less than 70°. An angle in the range of from 30 to 80° is preferred, more preferably from 40 to 75°, still more preferably from 50 to 70°. In one embodiment, the acute angle is from 55 to 65°, more preferably about 60°.

In one embodiment of the scissors, the scissor members each have the blade and handle extending along a single straight line, with the guide member extending at an angle to both the blade and the handle. In an alternative embodiment, the scissor members each have the blade extending at an angle to the handle member, with the guide member extending at an angle to the blade and being aligned to extend along or be parallel to the longitudinal axis of the handle. In a further alternative embodiment, the guide member extends at an angle to both the blade and the handle member of the scissors member to which it is attached or from which it extends.

Generally, the handles and blades of the scissors lie substantially in a single plane. The guide member may extend in a distal direction from the scissor member in the same plane as the plane of the blade and handles of the scissors. This arrangement may be preferred in embodiments where the blades of the scissor members extend at an angle to their respective handles. In this way, the blades of the scissors of this embodiment are more easily oriented relative to the tissue in which the incision is to be formed.

Alternatively, the guide member extends at an angle to the blade at an acute angle to the plane of the blade and handles of the scissors. In this way, the blades of the scissors of this embodiment are more conveniently oriented relative to the tissue to be cut, when the guide member is properly aligned. This in turn facilitates the use of the scissors by the medical practitioner. The guide member may extend at any suitable angle to the plane of the scissors. Preferably, this angle is at least 20°, more preferably at least 30°, still more preferably at least 40°. This angle is preferably less than 80°, more preferably less than 70°, still more preferably less than 60°. An angle in the range of from 20 to 80° is preferred, more preferably from 30 to 70°, still more preferably from 40 to 60°. In one embodiment, the acute angle is from 35 to 50°, more preferably about 45°.

The guide member may be integrally formed with the scissor member of the scissors. More preferably, the guide member is formed separately therefrom and attached to the blade. Any suitable means of attaching the guide member to the scissors may be used. Welding, for example laser welding, is particularly preferred.

The guide member may extend from either scissor member of the scissors. The selection of the scissor member to which the guide member is mounted may be determined, for example, by whether the scissors are to be left-handed or right-handed. Generally, surgical scissors comprise two scissor members, each consisting of a handle portion and a blade portion. The two components are pivotably connected, at the union of the handle portion and blade portion of each component. Typically, the pivot connection is formed using a screw. Preferably, the guide member extends from the scissor member on the opposing side of the scissors to the head of the screw. This is particularly the case where the guide member is attached to the scissor member by welding, especially by laser welding.

The guide member may be formed of any suitable material. Most preferably, the guide member is formed of the same material as the scissors. Suitable materials for forming surgical scissors are well known in the art. This is typically stainless steel.

Embodiments of the guide of the present invention will now be described, by way of example only, having reference to the accompanying figures, in which.

Figure 1:
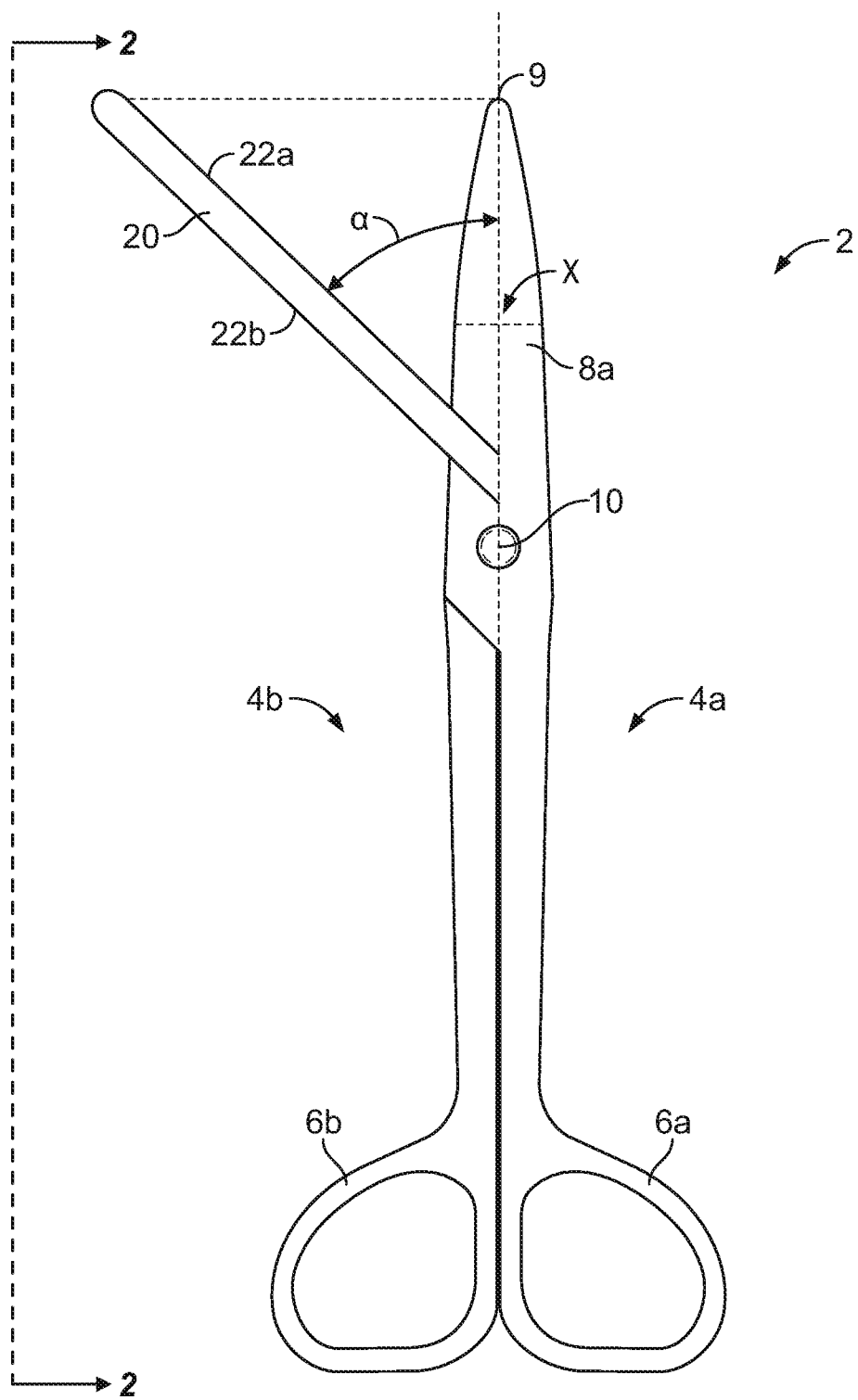
FIG. 1 is a plan view of a scissors according to one embodiment of the present invention.

Referring to FIG. 1, there is shown an episiotomy scissors, generally indicated as 2. The scissors 2 comprises two scissor members 4a, 4b, each consisting of a handle 6a, 6b and a blade 8a, 8b. The scissor members 4a, 4b are pivotally connected by way of a screw 10, in conventional manner. The scissor members are formed of stainless steel. The configuration of the scissor members 4a, 4b is generally conventional and common to surgical scissors. In particular, the handle and blade of each scissor member extend along a single straight line, as shown in FIG. 1.

A guide member 20 extends from one blade 8a and is in the form of a strip of stainless steel. The guide member 20 is attached at one end to the blade 8a by laser welding. The guide member 20 has opposing edge surfaces 22a, 22b.

Figure 2:
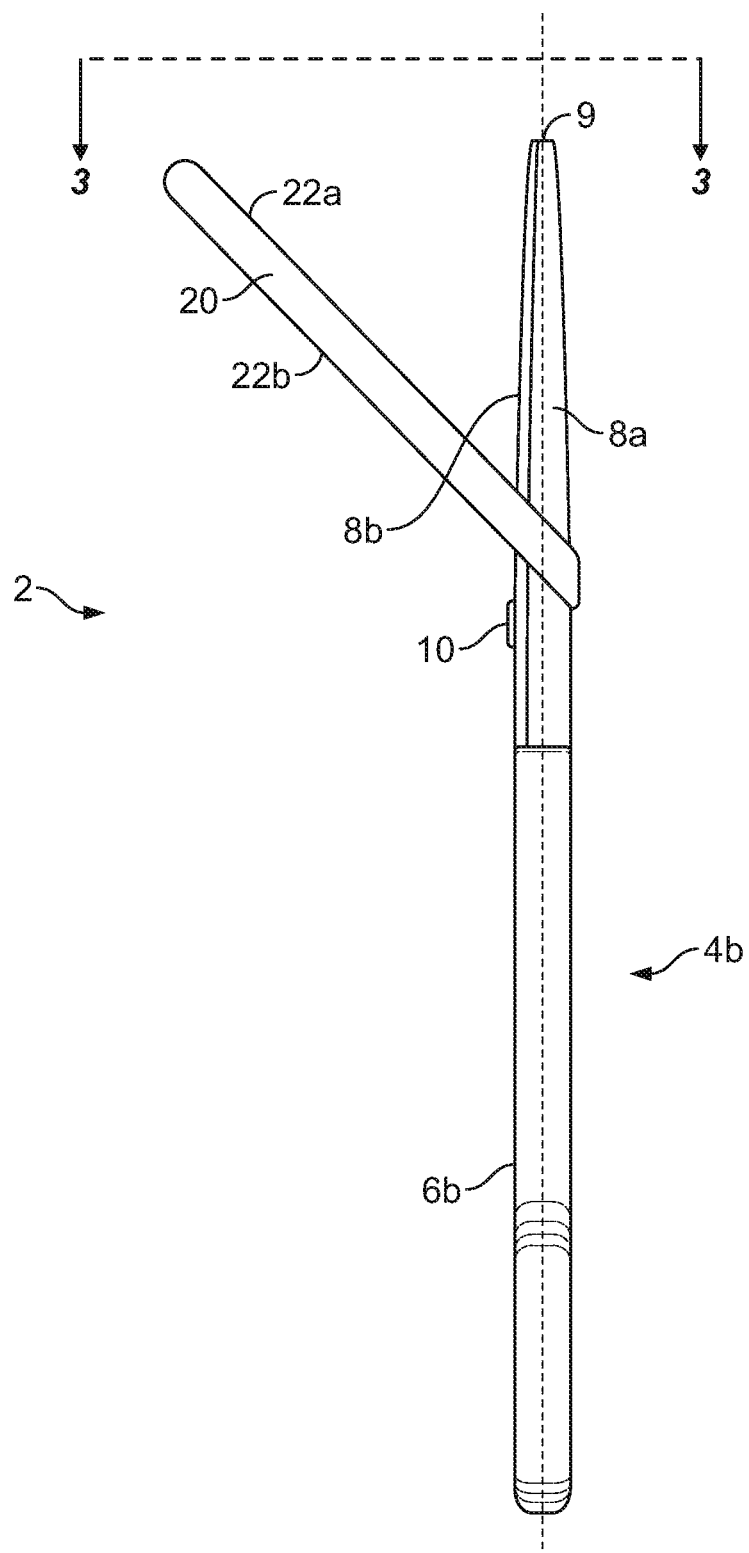
FIG. 2 is a side view of the scissors of FIG. 1 along the line II-II.

The blade 8a has a midpoint X, that is the point mid way between the distal end or point 9 of the blade and the screw 10. As shown in FIGS. 1 and 2, the guide member 20 is attached to the blade 8a at a position approximately mid way between the screw 10 and the midpoint X of the blade 8a. This allows the guide member 20 to be attached to the blade at a position at least 50 mm from the distal end or tip 9 of the blade 8a.

Figure 3:
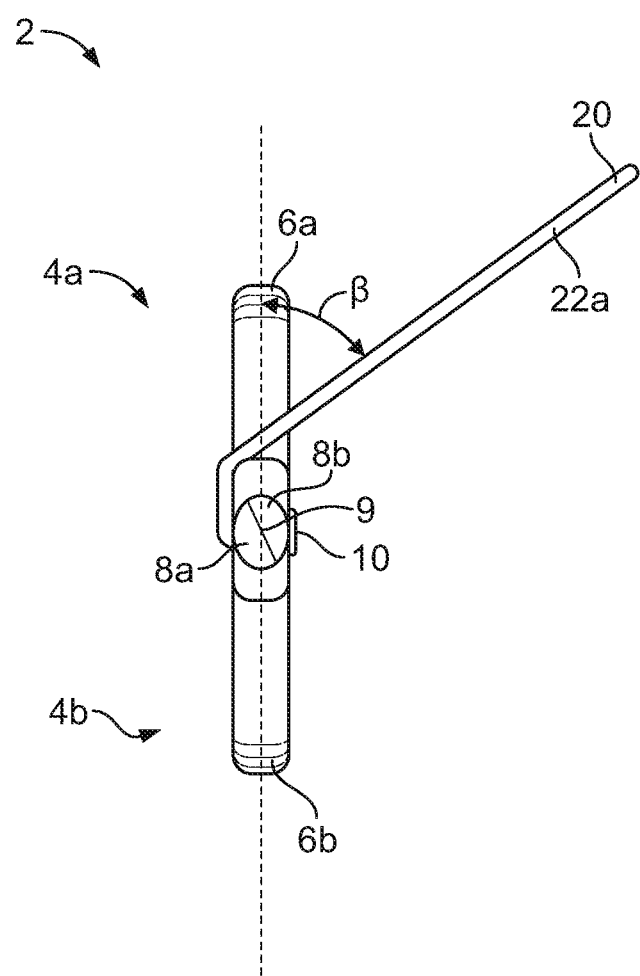
FIG. 3 is a front view of the scissors of FIG. 1 along the line III-III of FIG. 2.

As shown in FIGS. 2 and 3, the guide member is attached to the blade on the opposing side to the head of the screw.

As shown in FIG. 1, the guide member 20 extends from the blade 8a beyond the distal end of the blades, that is beyond the line drawn from the tip of the blades perpendicular to the longitudinal axis of the blades.

The guide member 20 extends in a distal direction away from the blade 8a at an acute angle α to the longitudinal axis of the blades, as shown in FIG. 1. In a preferred embodiment, the angle α is 60° (+/−2°).

Further, as shown in FIG. 3, the guide member 20 extends at an angle β to the plane of the scissors. In a preferred embodiment, the angle β is 45° (+/−2°).

In use, the guide member 20 is aligned with the midline of the perineum of the mother, such that the edge surfaces 22a, 22b extend to either side of the midline. The blades 8a, 8b of the scissors are thus angled to perform a mediolateral incision in the tissue surrounding the vaginal opening at the required angle.

Figure 4:
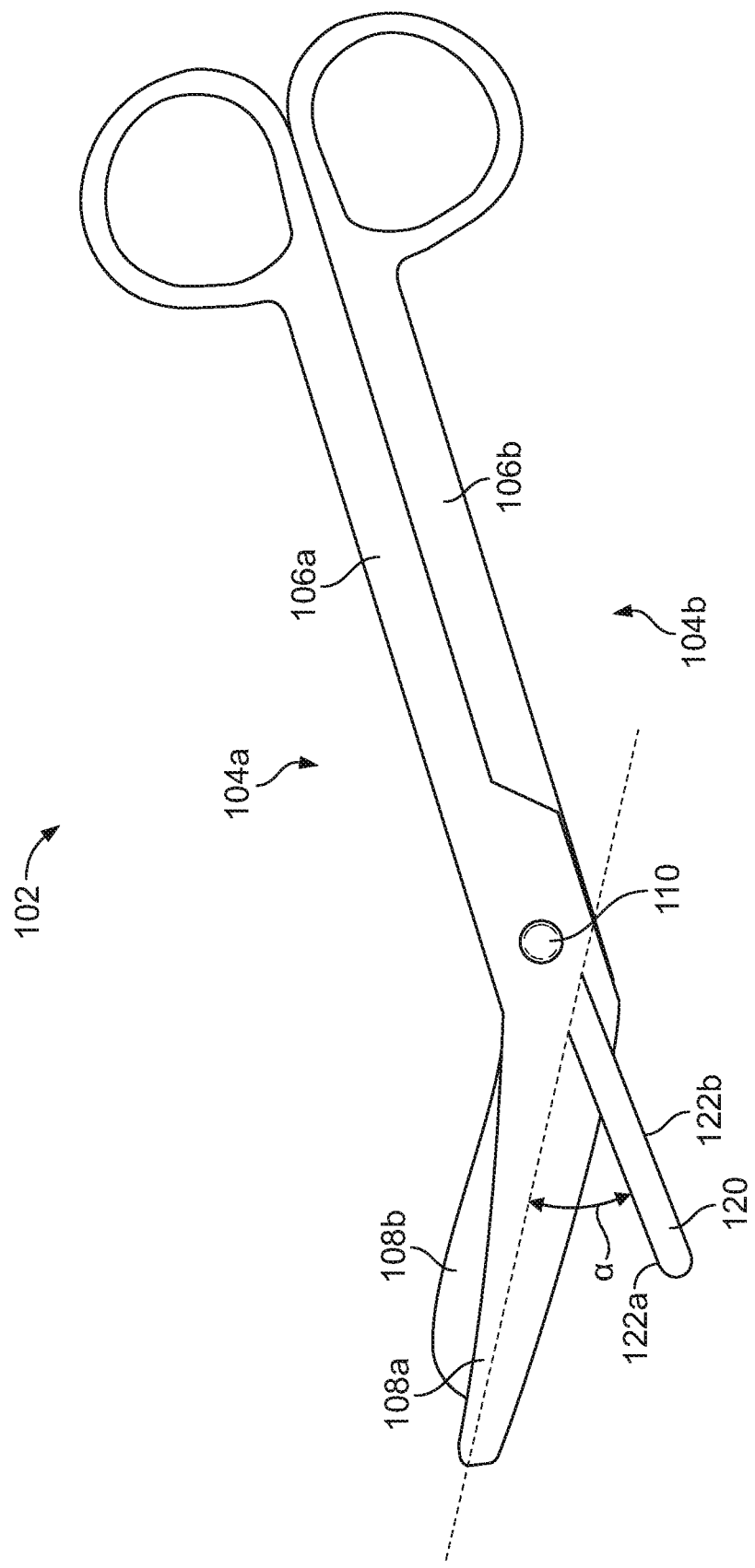
FIG. 4 is a plan view of a scissors according to a second embodiment of the present invention.

Turning to FIG. 4, there is shown a second embodiment of the scissors of the present invention, generally indicated as 102. The scissors 102 comprises two scissor members 104a, 104b, each consisting of a handle 106a, 106b and a blade 108a, 108b. The scissor members 104a, 104b are pivotally connected by way of a screw 110, in conventional manner. The scissor members are formed of stainless steel.

As shown in FIG. 4, the handles 106a, 106b extend at an angle to the respective blades 108a, 108b. The configuration of the scissor members 104a, 104b is generally conventional and common to surgical scissors.

A guide member 120 extends from one blade 108a and is in the form of a strip of stainless steel. The guide member 120 is attached at one end to the blade 108a by laser welding. The guide member 120 has opposing edge surfaces 122a, 122b.

The guide member 120 is attached to the blade 108a in the region of its proximal end, that is the end opposite the tip 109 of the blade and adjacent the handle 106a. As shown in FIG. 4, the guide member 120 is aligned with the handle 106a, such that the guide member and the handle extend along a single straight line.

As with the embodiment of FIGS. 1 to 3, the guide member is attached to the blade on the opposing side to the head of the screw.

The guide member 120 extends in a distal direction away from the handle 106a at an acute angle α to the longitudinal axis of the blade, as shown in FIG. 4. In a preferred embodiment, the angle α is 60° (+/−2°).

The guide member 120 extends in substantially the same plane as the plane of the two scissor members 104a, 104b.

Use of the scissors 102 is analogous to the use described above with respect to the embodiment of FIG. 1.

Figure 5:
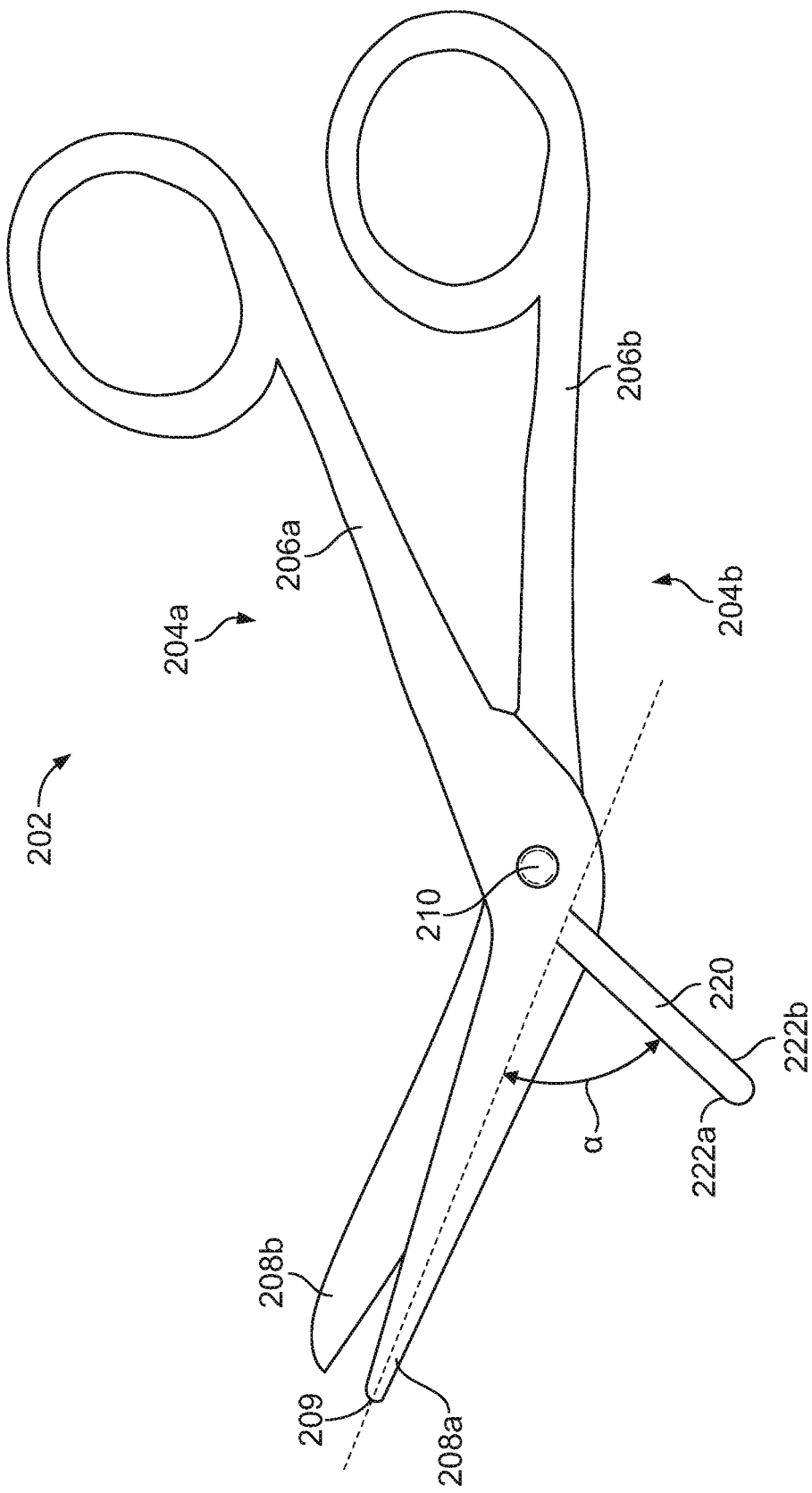
FIG. 5 is a plan view of a scissors according to a third embodiment of the present invention.

Turning to FIG. 5, there is shown a further embodiment of the scissors of the present invention, generally indicated as 202. The scissors 202 comprises two scissor members 204a, 204b, each consisting of a handle 206a, 206b and a blade 208a, 208b. The scissor members 204a, 204b are pivotally connected by way of a screw 210, in conventional manner. The scissor members are formed of stainless steel.

As shown in FIG. 5, the handles 206a, 206b extend at an angle to the respective blades 208a, 208b. The configuration of the scissor members 204a, 204b is generally conventional and common to surgical scissors.

A guide member 220 extends from one blade 208a and is in the form of a strip of stainless steel. The guide member 220 is attached at one end to the blade 208a by laser welding. The guide member 220 has opposing edge surfaces 222a, 222b.

The guide member 220 is attached to the blade 208a in the region of its proximal end, that is the end opposite the tip 209 of the blade and adjacent the handle 206a. As with the embodiment of FIGS. 1 to 3, the guide member is attached to the blade on the opposing side to the head of the screw.

The guide member 220 extends in a distal direction away from and at an angle to the handle 206a, so as to form an acute angle α to the longitudinal axis of the blade 208a, as shown in FIG. 5. In a preferred embodiment, the angle α is 60° (+/−2°).

The guide member 220 extends in substantially the same plane as the plane of the two scissor members 204a, 204b.

Use of the scissors 202 is analogous to the use described above with respect to the embodiment of FIG. 1.

The invention claimed is:

1. A method of performing an episiotomy on a subject, the subject having a vaginal opening, a perineum, and a perineal midline extending between the vaginal opening and the perineum, the method comprising:
    providing a scissors, comprising:
        a pair of scissor members connected at a pivot connection, the scissor members lying in a scissor plane defined thereby, each scissor member comprising a handle extending in a proximal direction from the pivot connection and a blade extending in a distal direction from the pivot connection, the distal direction being generally opposite the proximal direction; and
        a rod-shaped guide member having a guide member proximal end and a guide member distal end opposite the guide member proximal end, the guide member being mounted at its guide member proximal end to one of the scissor members at a first angle with respect to a longitudinal axis of the blade of the one of the scissor members,
    wherein the blade of the one of the scissor members has a mid-point mid-way between the pivot connection and a distal end of the blade opposite the handle, the guide member being mounted at a position on the blade of the one of the scissor members between the mid-point and the pivot connection,
    wherein the guide member has a length and a width, a ratio of the length to the width defining an aspect ratio of at least 5, and
    wherein the first angle is at least 30°; and
    aligning the guide member of the scissors with the perineal midline of the subject and making a lateral incision from the vaginal opening of the subject in a lateral direction away from the perineal midline.

2. The method according to claim 1, wherein the lateral incision is made in a single cut of the scissors.

3. The method according to claim 1, wherein, when viewed along the scissor plane, the guide member extends at a second angle to the scissor plane.

4. The method according to claim 1, wherein the guide member is flexible.

* * * * *